United States Patent [19]

Kim

[11] Patent Number: 5,173,219
[45] Date of Patent: Dec. 22, 1992

[54] UNIFORM SPHERICAL MULTILAMELLAR LIPOSOMES OF DEFINED AND ADJUSTABLE SIZE DISTRIBUTION

[75] Inventor: Sinil Kim, Solana Beach, Calif.

[73] Assignee: Research Development Foundation, Carson City, Nev.

[21] Appl. No.: 514,665

[22] Filed: Apr. 25, 1990

Related U.S. Application Data

[63] Continuation-in-part of Ser. No. 111,695, Oct. 21, 1987, abandoned, which is a continuation-in-part of Ser. No. 828,667, Feb. 12, 1986, abandoned.

[51] Int. Cl.$^5$ .......................... A61K 9/127; B01J 13/04
[52] U.S. Cl. ........................................ 264/4.6; 424/1.1; 424/450; 428/402.2; 436/829
[58] Field of Search ...................... 264/4.6; 428/402.2; 424/450; 436/829

[56] References Cited

U.S. PATENT DOCUMENTS

| | | | |
|---|---|---|---|
| 3,830,750 | 8/1974 | Wellman | 428/402.2 X |
| 4,235,871 | 11/1980 | Papahadjopoulos et al. | 264/4.6 X |
| 4,394,372 | 7/1983 | Taylor | 424/85 |
| 4,752,572 | 6/1988 | Sundberg et al. | 428/402.2 X |

OTHER PUBLICATIONS

Kim et al.: "Preparation of Multilamellar Vesicles of Defined Size-Distribution by Solvent-Spherule Evaporation", *Biochimica et Biophysica Acta*, 812 (1985) 793-801, Feb. 14, 1985.

*Primary Examiner*—Richard D. Lovering
*Attorney, Agent, or Firm*—James F. Weiler

[57] ABSTRACT

An improved, rapid method for preparing substantially spherical multilamellar liposomes of a defined and adjustable size within the range of 2 to 100 micrometers, suitable for encapsulation and targeting of drugs.

10 Claims, No Drawings

UNIFORM SPHERICAL MULTILAMELLAR LIPOSOMES OF DEFINED AND ADJUSTABLE SIZE DISTRIBUTION

CROSS REFERENCE TO RELATED APPLICATIONS

This application is a continuation-in-part of application Ser. No. 111,695, filed on Oct. 21, 1987 now abandoned, which application is a continuation-in-part of application Ser. No. 828,667 filed on Feb. 12, 1986 now abandoned, the disclosures of which are incorporated herein by reference.

DESCRIPTION

TECHNICAL FIELD OF THE INVENTION

The present invention relates to the production of synthetic multilamellar lipid vesicles, or liposomes useful for targeting drugs or vaccines.

BACKGROUND OF THE INVENTION

Among the problems encountered in conventional drug use today are loss of hair, diarrhoea and suppression of the immune response system in cancer chemotherapy, persistence of intracellular microbial infections in anti-microbial therapy, accumulation of toxic metals in tissues, and ineffectiveness of many vaccines. Indiscriminate drug action against target and normal cells, inability of drugs to penetrate body areas requiring treatment, and premature drug elimination or inactivation can explain some of these effects.

Approximately twenty five years ago it was discovered that mixing dry phospholipids with water results in the spontaneous formation of spherules containing bilayers of phospholipid molecules resembling biological membranes. As these spherules form, they entrap any water soluble substances that may be present into vesicular voids. Lipid-soluble substances, on the other hand, are incorporated into the liposomal membrane. Because incorporation into the aqueous or lipid phase is passive, no special methods have to be tailored for various substances to be incorporated. Virtually any substance, regardless of charge, solubility or other characteristics, can be incorporated into liposomes.

Liposome instability can arise when stored vesicles collide and fuse to form large liposomes. In vivo, these large vesicles will be removed from the circulation much more rapidly than small liposomes. This fusion of small liposomes can be reduced by imparting a net negative charge to the spherules. Drug loss due to leakage from liposomes can be reduced by incorporating excess cholesterol into the membrane.

Liposomes have been contemplated as being be a promising means for encapsulating a variety of substances to be delivered in vivo to patients, including drugs useful in cancer chemotherapy. For liposomes to be beneficially employed in these situations, it is necessary that they be manufactured in specific shapes and sizes, and also maintain stability during subsequent administration. Thus, there has been, and continues to be, considerable effort expended toward the development of suitable methods for producing liposomes having these medically useful properties.

There exist at least three classes of liposomes; unilamellar liposomes, multilamellar liposomes, and multivesicular liposomes. Multivesicular liposomes are spheroids having multiple, separate internal compartments formed from septa of lipid bilayers. Unilamellar liposomes consist of single spheroid bilayers. Multilamellar liposomes, on the other hand, are spheroids having multiple concentric bilayers. Bangham, et al. in the *Journal of Molecular Biology*, Volume 13, pages 238–252 (1965), described some of the general methods for making multilamellar liposomes as well as their properties. Huang in *Biochemistry*, Volume 8, pages 344–352 (1969), described unilamellar liposomes. Similarly, Kim et al. in *Biochem. Biophys. Acta.*, Volume 646, pages 1–10 (1981), described a novel method for producing unilamellar liposomes. The properties and problems associated with manufacturing multivesicular liposomes were also described by Kim et al. in *Biochem. Biophy. Acta.*, Volume 782, pages 339–348 (1983).

In addition to the above references, numerous other references describing methods for producing non-multilamellar liposomes exist. These include U.S. Pat. Nos. 4,078,052 and 4,235,871, issued to Papahadjopoulos; U.S. Pat. No. 4,224,179, issued to Schneider; U.S. Pat. No. 4,310,506, to inventor Baldeschwielder; and U.S. Pat. No. 4,522,803, issued to Lenk.

In U.S. Pat. No. 4,394,372, inventor Taylor discloses a method for making unilamellar liposomes. This method also yields some form of contaminating multilamellar structures not well described by the patentee. A shortcoming of the procedure for production of multilamellar structures is that the size distribution of multilamellar structures in Taylor's method is not adjustable, thus decreasing the flexibility of using this type of liposome as a drug delivery vehicle.

In addition to the above drawbacks, the Taylor method has the limitation that it is not specifically designed for making multilamellar liposomes. Furthermore, the process requires the use of a narrowly defined two-compound organic solvent system where one solvent is hydrophilic and the other is hydrophobic. The former must have a high partition coefficient in aqueous solutions, but must not dissolve in the latter. The latter must not totally dissolve the lipid membrane components by itself, but the membrane components must be completely soluble in the mixed solvent system. Together, the component system must form an interface with the aqueous solution.

Methods of preparing multilamellar liposomes are described in the literature. However, all of these methods have limitations which restrict their successful implementation in the medical arena. Perhaps the best known method is that of Bangham et al., *Journal of Molecular Biology*, Volume 13, pages 238–252 (1965). This method consists of first solubilizing a suitable lipid composition in an organic solution, then forming a dry layer of the lipid composition by removing the organic solvent, generally under vacuum, and hydrating the lipid composition using a suitable aqueous solvent followed by mechanically forming multilamellar liposomes with a sonicator or vortexer to disperse the semisolid lipid particles. A modification of this method, described in U.S. Pat. No. 4,485,054, consists of depositing the lipids on the surface of glass beads or other inert materials. Subsequent agitation more efficiently forms multilamellar liposomes.

In addition to the above, U.S. Pat. No. 4,308,166, issued to Marchettei, describes the preparation of liposomes by the addition of a phospholipid emulsion to a lyophilized, or otherwise dried, active substance. In U.S. Pat. No. 4,508,703, inventor Redziniak describes a method of preparation of multilamellar vesicles comprising atomizing lipids by dissolving them in a volatile organic solvent. The lipids are sprayed onto a suitable surface and then hydrated to form liposomes. Finally, Szoka, et al., *Annual Review of Biophysics and Bioengineering*, Volume 9, pages 467-508 (1980), presents a comprehensive review of methods and problems associated with the production of liposomes.

Although a survey of the literature makes it apparent that there are numerous ways of preparing liposomes having different physical properties, it is also apparent that each of these methods, and the liposomes produced, have certain technical drawbacks that prevent implementing them in the medical arena as vehicles for transporting drugs to particular body sites. Perhaps the major difficulty, particularly related to the generation of multilamellar liposomes, is the inability to precisely and reproducibly control the average multilamellar liposome size over a wide range. As alluded to above, the size of the liposome is crucial in many instances.

Although numerous attempts have been made to solve the above mentioned shortcomings, the efficiency and predictability required for medical applications has thus far not been achieved.

SUMMARY OF THE INVENTION

One aspect of this invention is an improved method for producing multilamellar liposomes of substantially spherical shape and adjustable average size. The liposomes produced by this method are substantially uncontaminated with unilamellar vesicles or multivesicular liposomes. This method comprises the steps of completely dissolving an amount of membrane-forming materials containing one or more amphiphatic lipid components in a hydrophobic organic solvent and then forming an 'oil-in-water' emulsion by placing the hydrophobic solution containing the lipid components under surface of a low ionic strength aqueous solution containing an amount of carbohydrate and agitating the admixture for a time sufficient to produce spherules of a desired size. At least one of the component lipids must be capable of imparting a net negative charge to the spherules formed. This emulsion is slowly admixed into an aqueous solution of ionic strength greater than 0.005 units, while simultaneously evaporatively removing the hydrophobic organic solvent.

In one embodiment, at least one of the lipid components is a phospholipid selected from the group consisting of phosphatidylcholine, cardiolipin, phosphatidylethanolamine, sphyngomyelin, lysophosphatidylcholine, phosphatidylserine, phosphatidylinositol, phosphatidylglycerol, and phosphatidic acid.

In another embodiment, the lipid emulsion further contains cholesterol to promote stability and reduce leakage.

In a preferred embodiment, the hydrophobic organic solvent is selected from the group consisting of diethyl ether, isopropyl ether, tetrahydrofuran, halogenated hydrocarbons, halogenated ethers, and esters. The low ionic strength aqueous solution includes water and about 5 percent carbohydrate.

In a particularly preferred embodiment, the multilamellar liposomes produced are substantially spherical in shape, and the average size of the multilamellar liposomes is within the range of 2 to 100 micrometers.

DETAILED DESCRIPTION OF THE INVENTION

The general procedure for making multilamellar liposomes having a spherical configuration, and adjustable size, initially involves forming substantially non-coalescing spherules by dissolving a suitable lipid mixture in an organic solvent and combining this solution with a low ionic strength aqueous solution, thereby forming an emulsion containing non-coalescing lipid spherules suspended in the aqueous phase. The emulsion is then subjected to evaporation, causing the organic solvent to be removed under conditions described below, which yields the desired liposomes. By spherules is meant droplets of organic solvent suspended in an aqueous solution having lipid material associated therewith.

In order to form multilamellar liposomes of a spherical configuration and variable size, I have found that the lipid mixture should contain an amphiphatic lipid having a net negative charge. The amount of charged lipid will vary depending on the type of lipid used, ionic strength, pH, etc. However, it is important to note that the liposome can consist of 100% amphiphatic lipids with a net negative charge.

Aside from this requirement, the lipids present in the multilamellar liposome may be varied with respect to such parameters as the degree of branching as well as the length of the fatty acid side chains. Most often, however, lipids will be selected from those previously described in the literature, which have been used to prepare different types of liposomes.

Preferably, the lipids chosen will be non-immunogenic and biodegradable, considering their anticipated use in patients. Consequently, it is anticipated that phospholipids such as the lecithins, both natural and synthetic, are a preferred lipid species. Such compounds include ovo-or-egg-yolk phosphatidyl choline, or lecithin, which consists substantially of lipids containing $C_{1-6}C_{1-8}$hydrocarbon residues with about half of these residues containing one double bond. Also included are the synthetic lecithins:

di-(tetradecanoyl) phosphatidylcholine,
di-(hexadecanoyl) phosphatidylcholine,
di-(octadecanoyl) phosphatidylcholine,
di-(oleyl) phosphatidylcholine, and
di-(linoleyl) phosphatidylcoline.

It is worth noting that a consideration in choosing a suitable lecithin for preparation of the multilamellar vesicles is the phase transition temperature of the lecithin. Lipids having a phase transition temperature less than physiological temperature, and preferably also less than the temperature at which the vesicles are prepared will most often be employed. Consequently, the lower phase transition temperature of natural egg lecithins and synthetic analogs and derivatives thereof make these of special interest.

As alluded to above, in addition to the basic phospholipid component of the multilamellar liposomes, the liposomes will also contain preferably about a 1% molecular ratio of an amphiphatic lipid having a net negative charge. Alternatively, the liposomes can consist of 100% net negatively charged lipids. Examples of the latter include phosphatidic acid, dicetyl phosphate, phosphatidyl serine, phosphatidyl glycerol, and the more complex gangliosides found in the brain. Substances such as cardiolipin may also be utilized.

A further component that may be employed in construction of the multilamellar liposomes is a lipid condensing agent. The most common example is cholesterol, which also has a restricting effect on the mobility of the lipid side chains, thereby lowering the permeability of the liposomes to materials to be encapsulated.

The subject multilamellar liposomes can be constructed by first dissolving the lipid components which will form the liposome in a suitable organic solvent that can be removed from the lipid composition when desired. Representative examples of such solvents include a wide variety of ethers, esters, ketones, hydrocarbons, including aromatic and aliphatic fluorocarbons, and silicones in which an aqueous phase does not have an appreciable solubility. It will, of course, be understood by those skilled in the art that the solvents may be used either alone or in admixture, but preferably alone.

As will be discussed in more detail below, and as will be appreciated by those studied in the art, for each solvent or admixture of solvents to be employed, the optimal ratio of lipid and solvent will be determined on a case by case basis. The emulsion is made by combining the lipid-organic solvent solution with an aqueous solution followed by agitation to form substantially non-coalescing spherules. The aqueous solution must have a very low ionic strength, preferably zero ionic strength, in order to form substantially non-coalescing spherules and prevent total separation of the organic and aqueous phases that comprise the emulsion. The amount of aqueous phase utilized will vary depending on the amount of organic solution used. Prior to evaporation, the mixture is agitated employing any of a number of techniques, preferably vortexation, sonication, or other suitable means. The duration of agitation is for a time sufficient to produce readily visible spherules suspended in the aqueous phase after the two phases have separated following agitation.

The organic solvent is removed by evaporation, which can conveniently be accomplished by flushing nitrogen or air over the surface of the aqueous phase at temperatures generally between 20°-60° C. The evaporative conditions will strongly depend upon the physical properties of the organic solvent, and the lipid materials used in the formulation of the multilamellar liposomes. Such conditions are well known to those skilled in the art.

An aspect of the subject invention that facilitates the formation of spherical multilamellar liposomes is the presence of an aqueous solution having appreciable ionic strength in contact with the emulsion while it is undergoing evaporation. If the ionic strength of the emulsion is not increased during the evaporation step the result is the formation of non-spherical liposomes, particularly small non-spherical unilamellar liposomes. Thus, it will be appreciated that while the initial multilamellar liposome forming step requires mixing an organic solution containing the necessary lipid components with an aqueous solution of low ionic strength, that subsequently the evaporation step critically requires an increase in the ionic strength of the emulsion mixture in order to form spherical multilamellar liposomes. Although a number of techniques to increase the ionic strength of the emulsion may be employed, I have found that a preferred method is to add the emulsion dropwise into a high ionic strength solution in the evaporation chamber. The increase in ionic strength during the evaporation step prevents the deformation of multilamellar liposomes, and also prevents the formation of unilamellar liposomes. Lastly, the emulsion should be slowly added to the high ionic strength aqueous phase, which additionally prevents coalescence of the spherules by rapid evaporation of the organic solvent.

The size of the multilamellar liposomes can be increased or decreased merely by altering the concentration of lipid dissolved in the organic solvent, as well as by varying the duration of agitation. The average size of multilamellar liposomes, expressed as mean liposome volume, as assayed by light microscopy varies linearly with the concentration of lipid that is used to prepare the liposomes. Consequently, doubling of the lipid materials results in about a doubling of the mean liposome volume.

EXAMPLE 1    LIPOSOME PREPARATION

1. Preparation of Chloroform-Diethyl Ether Spherules.

One and one-half (1.5) ml of 5% (w/v) glucose was placed in a clean one-dram glass vial. In another container, 3-48 umol of amphiphatic lipids and any lipid-soluble substance to be incorporated into vesicles were completely dissolved in 50 ul of chloroform and 50 ul of diethyl ether. The lipid phase was placed under the surface of a 5% low ionic strength glucose solution in the vial with a glass capillary pipet. The vial was immediately closed with an aluminum foil-lined screw cap, attached horizontally to the head of the vortex machine with a piece of an adhesive paper tape and agitated for 5-75 seconds to produce small chloroform-diethyl ether lipid-containing spherules suspended in 5% glucose solution.

2. Evaporation of Chloroform and Diethyl Ether to Form Vesicles.

One and one-half (1.5) ml of a 5% glucose solution and 0.5 ml of 0.9% NaCl solutions were placed on the bottom of a 50 ml Erlenmeyer or filtration vacuum flask. A stream of nitrogen gas at 5 l/min was introduced into the flask via a piece of glass tubing protruding 3 cm into the mouth of the flask. The spherules suspended in 5% glucose solution were carefully added to the solution in the flask with a Pasteur pipet one drop at a time over a 5 min period. Throughout the evaporation process, the flask was gently swirled, care being taken to keep the bottom of the flask covered with the liquid. The flask was kept in a water bath at 37° C. The solvent evaporation was then allowed to proceed for 2 more min. The volatile organic solvents were evaporated completely. No odor of chloroform or diethyl ether was detectable at this time. Water-soluble substances to be incorporated into the vesicles were added, both, to the 1.5 ml of 5% glucose solution at the chloroform-diethyl ether spherule preparation step and to the aqueous solution in the flask at the solvent evaporation step. The concentrations of the substances to be incorporated were the same in both steps.

3. Liposome Characterization a. Determining the Size Distribution

The multilamellar vesicle preparations were wet mounted without dilution in a hemacytometer and photographed on a Zeiss photomicroscope. The negatives were projected onto a piece of paper by using a photographic enlarger, with the magnification adjusted to 1000×. Diameters($d_i$) of 395-1247 vesicles were measured for each preparation and assigned to the nearest 1 m-size group (i). The volume ($V_i$) occupied by vesicles in each size group was obtained by multiplying the number ($n_i$) of vesicles in each size group by the volume of a sphere ($\pi d^3/6$) of the same diameter. The vesicle volume of each size group ($V_i$) was then divided by the sum of the volumes ($_iV_i$) and multiplied by 100 to obtain percent of total volume, $v_i=(V_i/_iV_i)\times 100$. From volume-normalized size distribution ($v_i$ versus $d_i$), the mean diameter (d) and standard deviations were calculated.

b. Determining the Optical Volume

A useful parameter is the amount of vesicle volume produced by a given mass of lipid. The optical volume ($V_{op}$) was defined as the quotient of the sum of the vesicle volumes above ($_iV_i$) (extrapolated to the total preparation) and the mass of lipid (M) used in a given preparation.

$$V_{op}=(V_i)\cdot(V_t/V_h)\cdot(1/M)$$

where $V_t$ is the total volume of the vesicle preparation, (suspending medium plus vesicles) and $V_h$ is the volume of the hemacytometer chamber. $V_{op}$ quantitates the volume occupied by vesicles that are visible under the light microscope (greater than about 1 μm in diameter) per unit amount of lipid used.

4. Determining Excluded Volume

Liposomes were prepared with the lipid combination DOPC/cholesterol/DMPG at 9:9:2 molar ratio at the lipid concentration of 30 mg in 100 l of solvents. The duration of mechanical agitation was 15 s. At the end of the solvent evaporation, $^{14}$C-labeled glucose was added to the preparation and mixed with 9-fold volume of 0.3M sucrose solution. The liposomes were then floated to the top of the centrifuge tube in a Beckman preparative ultracentrifuge (Model L5-75B) at 61,000×g for 30 min. The clear suspending medium in the bottom was separated from the floating liposome fraction with a syringe and hypodermic needle piercing the centrifuge tube. The excluded volume was calculated from the equation:

$$V_{ex} = \frac{C_m - C_1 \cdot V_1}{C_m M}$$

where $C_m$ represents the d.p.m. of [$^{14}$C]glucose in 50 l of suspending medium, $C_1$ represents the d.p.m. of 50 l of liposome fraction (pellet), $V_1$ is the volume of the liposome fraction, and M is the amount of lipid in the liposome fraction.

EXAMPLE 2 ADJUSTING LIPOSOME SIZE

To prepare smaller liposomes than those of Example 1, the amount of amphiphatic lipids used in the lipid phase were decreased. Alternatively, the duration of mechanical agitation was increased. Both maneuvers resulted in smaller liposomes being produced.

Increasing the amount of starting amphiphatic lipid material resulted in increased liposome size, as did a reduction in mechanical agitation.

It was found that the average liposome size (expressed as mean vesicle volume) as measured with a light microscope correlated linearly with lipid concentration, i.e., doubling the lipid concentration resulted in a doubling of liposome mean vesicle volume. It was also discovered that the mean diameter is the inverse square root function of the duration of shaking:

$$D=a+bT^{-\frac{1}{2}}$$

where D is the diameter in micrometers, T is the duration of shaking, and a and b are constants.

EXAMPLE 3 PREPARATION OF MULTILAMELLAR LIPOSOMES USING A SINGLE SOLVENT

Approximately 10 milligrams of amphiphatic lipids consisting of dioleoyl lecithin, cholesterol and dimyristoylphosphatidylglycerol, in a molar ratio of 9:9:2, were dissolved in 100 microliters of a single organic solvent, chloroform. The amphiphatic lipid-in-chloroform solution, was added to 1.5 ml of a low-ionic strength aqueous solution containing 5% glucose. The reaction vessel, a standard laboratory vial, was closed with a screw cap lined with synthetic resin polymers and products sold under the trademark TEFLON, attached to the head of a vortex machine with adhesive tape, and agitated at maximum speed for 15 seconds. This agitation resulted in the production of small chloroform spherules that were suspended in the 5% glucose solution, and readily discernable.

In order to evaporate the chloroform from the spherule-containing glucose solution without coalescing the spherules, 1.5 ml of an aqueous 5% glucose solution was added to 0.5 ml of an 0.9% sodium chloride solution and the mixture pipeted into a 50 ml Erlenmeyer flask. Subsequently, the chloroform spherule-containing glucose solution was taken up into a pipet and carefully added into the flask one drop at a time over a period of approximately 5 minutes, while the flask was flushed with nitrogen gas. As contents in the flask were being evaporated, the flask was swirled and kept under an atmosphere of nitrogen gas to prevent oxidation of unsaturated double bonds present in the phospholipids. The flask was kept at a temperature of about 37° C. by keeping it immersed in a warm waterbath. Within approximately 7 minutes total time, the organic phase had evaporated, leaving behind the aqueous phase containing the multilamellar liposomes.

EXAMPLE 4 PREPARATIONS UTILIZING OTHER LIPID COMPOSITIONS

Other amphiphatic lipid compositions, such as dioleoyl lecithin and cardiolipin in a molar ratio of 176:1, and dimyristoylphosphatidylcholine (DMPC) and dimyristoylphosphatidylglycerol (DMPG) in 1:1 molar ratio yielded satisfactory liposomes, as did other combinations or single lipids, for example, 100% cardiolipin. The only apparent constraints on the lipid composition were the presence of net-negatively charged amphiphatic lipid (to prevent coalescence of spherules) and solubility in the organic solvent used.

EXAMPLE 5 TRAPPING AND INCORPORATION OF SUBSTANCES INTO MULTILAMELLAR LIPOSOMES

To incorporate lipid-soluble substances, such as Sudan III, required dissolution of these materials in the lipid phase. As can be seen in Table 1, Amphotericin B was captured with an efficiency of 73%, and Sudan III was 74% using 11.3 mg of DMPC and DMPG in 7:3 and 1:1 molar ratios, respectively.

TABLE 1

VARIOUS MATERIALS INCORPORATED INTO VESICLES

11.3 mg (in 100 l of solvents) of the lipid combination DMPC/DMPG (1:1 molar ratio except for amphotericin B for which it was 7:3) were used in each preparation and the mechanical agitation was for 5 s. $V_{ex}$ and $V_{op}$ are defined in the text.

| Materials incorporated | Concn. | % of total volume | Volumes[c] l/mg | l/mol |
|---|---|---|---|---|
| Ponceau S | 17 g/ml | 1.3 | 4.0 | 2.7 |
| Glucose[a] | 5% (w/v) | | | |
| captured vol. | | 0.6 | 0.5 | 0.3 |
| optical vol. ($V_{op}$) | | 2.9 | 2.6 | 1.6 |
| excluded vol. ($V_{ex}$) | | 3.8 | 3.3 | 2.0 |
| Doxorubicin | 67 g/ml | 56 | 170 | 120 |
| Sudan III | 0.45 g/mg[b] | 74 | n.a. | |
| Amphotericin B | 89 g/mg[b] | 73 | n.a. | |

[a]30 mg (in 100 l of solvents) of DOPC/cholesterol/DMPG (9:9:2 molar ratio) were used with 15 s mechanical agitation (identical parameters as FIG. 3c). The difference in the captured volume compared to the encapsulation of glucose above was the result of entirely different experimental conditions in which the duration of mechanical shaking, the type and the amount of lipids used were different.
[b]Micrograms of material to be incorporated per milligram of lipids used, n.a., not applicable, the material is insoluble in water.
[c]Captured volumes unless otherwise specified.

Incorporation of water-soluble materials, such as doxorubicin, required dissolution in the 5% glucose aqueous phase and/or in the high ionic strength aqueous phase at the evaporation step. The capture efficiency of 67 ug doxorubicin, using 11.3 mg of DMPC and DMPG in 1:1 molar ratio was 56%.

Electron Microscopy

Electron microscopy was done on preparations of multilamellar liposomes to determine purity and integrity of the membrane structures. All preparations were substantially uncontaminated by unilamellar liposomes.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely, by the scope of the following claims.

What is claimed is:

1. An improved method for producing spherical multilamellar liposomes of adjustable average size, substantially uncontaminated with unilamellar vesicles, comprising the steps of:
   (a) completely dissolving an amount of membrane-forming materials containing one or more amphipatic lipid components, at least one of said components being capable of imparting a net negative charge, in one or more hydrophobic organic solvents, each of which is capable of totally dissolving said lipid components;
   (b) placing said hydrophobic solution containing said lipid components resulting from step (a) within a low ionic strength aqueous solution;
   (c) forming an oil-in-water emulsion from the hydrophobic solution and the aqueous solution and;
   (d) slowly adding said emulsion into an aqueous solution of ionic strength greater than 0.005 units, while simultaneously evaporatively removing said one or more hydrophobic organic solvents.

2. The method of claim 1 wherein at least one of said lipid components is a phospholipid.

3. The method of claim 1 wherein said one or more amphipatic lipid components are selected from the group consisting of phosphatidylcholine, cardiolipin, phosphatidylethanolamine, sphyngomyelin, lysophosphatidylcholine, phosphatidylserine, phosphatidylinositol, phosphatidylglycerol, and phosphatidic acid.

4. The method of claim 3 wherein said one or more amphipatic lipid components further contain cholesterol.

5. The method of claim 1 wherein said hydrophobic organic solvent is selected singly or in combination from the group consisting of diethyl ether, isopropyl ether, tetrahydrofuran, halogenated hydrocarbons, halogenated ethers, and esters.

6. The method of claim 1 wherein said low ionic strength aqueous solution includes water and about 5 percent carbohydrate.

7. The method of claim 1 wherein the average size of said multilamellar liposomes is adjustable within the range of 2 to 100 micrometers.

8. The method of claim 1 wherein the at least one biologically active lipophilic material is provided in admixture with the lipid component.

9. The method of claim 1 wherein the average size of the liposomes is determined by the amount of the lipid component used.

10. The method of claim 1 wherein the average size of the liposome is determined by the extent of emulsification in the "oil-in-water" emulsion formation from the hydrophobic solution and the aqueous solution.

* * * * *

UNITED STATES PATENT AND TRADEMARK OFFICE
CERTIFICATE OF CORRECTION

PATENT NO. : 5,173,219
DATED : December 22, 1992
INVENTOR(S) : Sinil Kim

It is certified that error appears in the above-indentified patent and that said Letters Patent is hereby corrected as shown below:

Column 1, line 53, "be" should be deleted.

Column 8, line 28, "an" should read -- a --.

Column 10, Claim 8, line 40, "wherein the at" should read -- wherein at --.

Signed and Sealed this

Twenty-fifth Day of January, 1994

Attest:

BRUCE LEHMAN

*Attesting Officer*  *Commissioner of Patents and Trademarks*